US008338089B2

(12) United States Patent
Yu et al.

(10) Patent No.: US 8,338,089 B2
(45) Date of Patent: Dec. 25, 2012

(54) METHOD OF INHIBITING LENTIVIRAL INFECTIVITY UTILIZING ZINC CHELATION TO INHIBIT VIF ACTIVITY

(75) Inventors: Xiao-Fang Yu, Baltimore, MD (US); Elana S. Erhlich, Baltimore, MD (US); Xiao Zuoxiang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1404 days.

(21) Appl. No.: 11/984,672

(22) Filed: Nov. 20, 2007

(65) Prior Publication Data

US 2008/0206357 A1    Aug. 28, 2008

Related U.S. Application Data

(60) Provisional application No. 60/860,197, filed on Nov. 20, 2006.

(51) Int. Cl.
  *C12Q 1/70*    (2006.01)
  *A61K 39/21*   (2006.01)
  *A61K 33/00*   (2006.01)
(52) U.S. Cl. ................... 435/5; 424/208.1; 424/600
(58) Field of Classification Search ............ None
  See application file for complete search history.

(56) References Cited

U.S. PATENT DOCUMENTS

| 5,082,851 | A | 1/1992 | Appelbaum et al. | |
| 6,323,218 | B1* | 11/2001 | Bush et al. | .................. 514/311 |
| 7,220,554 | B2 | 5/2007 | Kabat et al. | |
| 2004/0009951 | A1 | 1/2004 | Malim et al. | |

FOREIGN PATENT DOCUMENTS

| WO | WO-98/40071 | 9/1998 |
| WO | WO-2004/084799 A2 | 10/2004 |
| WO | WO-2004/084799 A3 | 10/2004 |
| WO | WO-2005/024422 A2 | 3/2005 |

OTHER PUBLICATIONS

Gait, M. J., and J. Karn. 1995. Progress in anti-HIV structure-based drug design. TIBTECH 13:430-438.*
Hirsch, M. S., et al. 1998. Antiretroviral drug resistance testing in adults with HIV infection. JAMA 279(24):1984-1991.*
Pope, M., and A. T. Haase. 2003. Transmission, acute HIV-1 infection and the quest for strategies to prevent infection. Nat. Med. 9(7):847-852.*
Van Rompay, K. K. A. 2010. Evaluation of antiretrovirals in animal models of HIV infection. Antivir. Res. 85:159-175.*
Mehle, A., et al. 2006. A zinc-binding region in Vif binds Cul5 and determines cullin selection. J. Biol. Chem. 281(25):17259-17265.*
Xiao Z, et al., 2006, Assembly of HIV-1 Vif-Cul5 E3 ubiquitin ligase through a novel zinc-binding domain-stabilized hydrophobic interface on Vif, Virol. 349:290-299.*
Xiao, Z., et al., 2007, Zinc chelation inhibits HIV Vif activity and liberates antiviral function of the cytidine deaminase APOBEC3G, FASEB J. 21:217-222.*
Xiao et al. (2007) "Zinc chelation inhibits HIV Vif activity and liberates antiviral function of the cytidine deaminase APOBEC3G.," FASEB J., vol. 21 (1), pp. 217-222.
Luo et al. (2005) "Primate lentiviral virion infectivity factors are substrate receptors that assemble with cullin 5-E3 ligase through a HCCH motif to suppress APOBEC3G." Proc Natl Acad Sci U S A, vol. 102 No. 32, pp. 11444-11449.
Xiao et al. (2006) "Assembly of HIV-1 Vif-Cul5 E3 ubiquitin ligase through a novel zinc-binding domain-stabilized hydrophobic interface n Vif." Virology, vol. 349, pp. 290-299.
Yu et al. (2003) "Induction of APOBEC3G Ubiquitination and Degradation by an HIV-1 Vif-Cul5-SCF Complex.", Science, vol. 302, pp. 1056-1060.
Sheehy et al. (2002) "Isolation of a human gene that inhibits HIV-1 infection and is suppressed by the viral Vif protein." Nature, vol. 418, pp. 646-650.
Harris et al. (2004) "Retroviral Restriction by APOBEC Proteins." Nat Rev Immunol, vol. 4, pp. 868-867.
Yu et al. (2004) "Selective assembly of HIV-1 Vif-Cul5-ElonginB-ElonginC E3 ubiquitin ligase complex through a novel SOCS box and upstream cysteines." Genes & Dev, vol. 18, pp. 2867-2872.
Mehle et al. (2004) "Phosphorylation of a novel SOCS-box regulates assembly of the HIV-1 Vif-Cul5 complex that promotes APOBEC3G degradation.", Genes & Dev, vol. 18, pp. 2861-2866.
Cohen, J. (2003) "Escape Artist Par Excellence.", Science, vol. 299, pp. 1505-1508.
Goncalves et al. (2002) "Functional neutralization of HIV-1 vif protein by intracellular immunizaiton inhibits reverse transcription and viral replication" Int Conf AIDS, vol. 14, abstract No. MoPeA3042. (Abstract only).
Travis, J. (2002) "Disabled Defense: HIV protein counters immunecell gene.". Science News, vol. 162, (3), p. 35.
Sheehy (2003) "The antiretroviral enzyme APOBEC3G is degraded by the proteasome in response to HIV-1 Vif." Nat Med., vol. 9 (11), pp. 1404-1407. (Abstract only).
Marin (2003) "HIV1 Vif protein binds the editing enzyme APOBEC3G and induces its degradation.", Nat Med., vol. 9 (11), pp. 1398-1403. (Abstract only).
The J. David Gladstone Institutes at the University of California, San Francisco (2006) "Why HIV Cannot Infect Resting CD4 T-Cells." http://www.gladstone.ucsf.edu/gladstone/site/publicaffairs/section.php?id=1485.

(Continued)

*Primary Examiner* — Jeffrey S. Parkin
(74) *Attorney, Agent, or Firm* — Johns Hopkins Technology Transfer

(57) ABSTRACT

The present invention relates, e.g., to a method for inhibiting infectivity of a lentivirus (e.g., a lentivirus which expresses a Viral infectivity factor (Vif) protein), such as, e.g., SIV, SHIV and/or HIV, comprising contacting a cell which is producing the virus with an antiviral-effective amount of a membrane-permeable Zinc (Zn) chelator, wherein the antiviral-effective amount of the Zn chelator does not substantially inhibit proteins in the cell which contain Zn-binding motifs other than lentivirus Vif. Kits and pharmaceutical compositions are also disclosed, as is a method for identifying inhibitors of lentiviruses that target a specific zinc-binding motif of the lentivirus Vif protein.

12 Claims, 4 Drawing Sheets

OTHER PUBLICATIONS

UTEK Knowledge Express (2004) "Putting Nobel Prize-Winning Proteasome Research To Use.", http://www.knowledgeexpress.com/recordview.asp?rid=80085&dbid=24&ListLoc=52& . . . .

Wainberg (2005) "Cellular Resistance to HIV: The Vif-APOBEC Connection." Medscape, http://www.medscape.com/viewarticle/500076.

Miller et al. (2000) "HIV VIf as a Therapeutic Target." National Institute of Allergy and Infectious Diseases; Division of AIDS, NIAID, Bethesda, MD, http://www.niaid.nih.gov/Daids/vif.htm.

Conticello et al. (2003) "The Vif protein of HIV triggers degradation of the human antiretroviral DNA deaminase APOBEC3G.", Curr Biol., vol. 13 (22), pp. 2009-2013. (Abstract only).

Lin et al. (1998), "Zinc Is Essential for Binding of $p56^{lck}$ to CD4 and CD8x*.", J Biol Chem, vol. 273, (49), pp. 32878-32882.

* cited by examiner

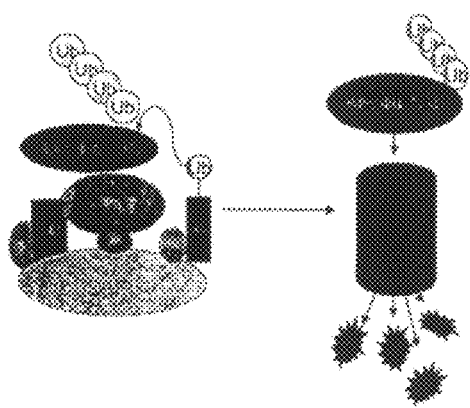
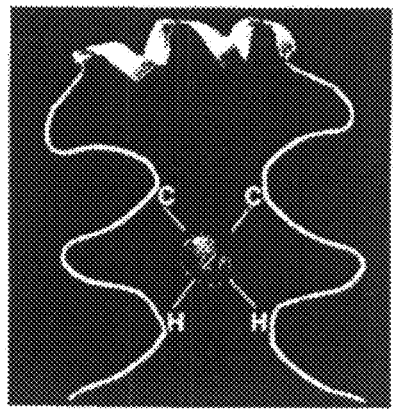
Fig. 1A
Fig. 1B
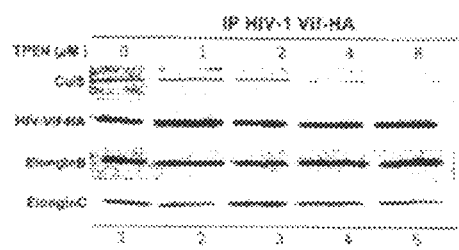
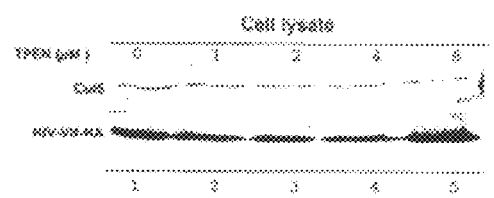
Fig. 1C
Fig. 1D

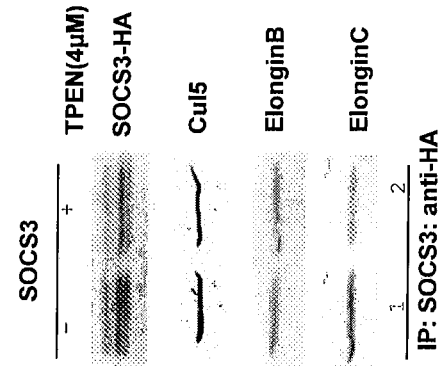
FIG. 2A
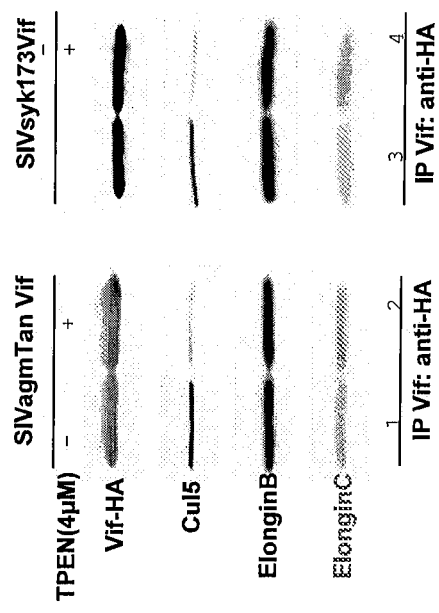
FIG. 2B
FIG. 2C

METHOD OF INHIBITING LENTIVIRAL INFECTIVITY UTILIZING ZINC CHELATION TO INHIBIT VIF ACTIVITY

This application claims the benefit of the filing date of U.S. provisional application 60/860,197, filed Nov. 20, 2006, which is incorporated by reference herein in its entirety.

This research was supported by a grant from the U.S. Department of Health and Human Services, NIAID NIH, number AI062644. The U.S. Government has certain rights in the invention.

FIELD OF THE INVENTION

This invention relates, e.g., to a method for inhibiting the infectivity of a lentivirus (e.g., SIV, SHIV and/or HIV). Kits and pharmaceutical compositions are also disclosed, as is a method for identifying inhibitors of lentiviruses that target a particular motif of the lentivirus Vif protein.

BACKGROUND INFORMATION

APOBEC3G (A3G) is a cellular antiviral protein that, when incorporated into a budding HIV-1 virion, dramatically reduces infectivity in the subsequent cell (see, e.g., Harris et al. (2004) Nat Rev Immunol 4, 868-877; Navarro et al. (2004) Curr Opin Immunol 16, 477-482; Turelli et al. (2005) Science 307, 1061-1065). However, A3G incorporation into the virion is dramatically reduced due to the action of the HIV-1 Vif protein. HIV-1 Vif hijacks the cellular ubiquitin proteasome system and targets A3G for proteasomal degradation (see, e.g., Yu et al. (2003) Science 302, 1056-1060; Marin et al. (2003) Nat Med 9, 1398-1403; Liu et al. (2005) J Virol 79, 9579-9587; Kobayashi et al. (2005) J Biol Chem 280, 18573-18578).

The Cullin E3 ubiquitin ligases are a family of modular RING E3 ligases that consist of three main components: a Cullin (Cul1,2,3,4a,4b,5, or 7), an adaptor protein, and a substrate receptor. The E3 ligase is the third enzyme in the ubiquitination sequence and is responsible for substrate specificity. Cullin acts as scaffolding upon which the adaptor protein and substrate receptor assemble in order to bring a specific substrate in close proximity to the E2 ubiquitin conjugating enzyme. The substrate receptor determines the specificity of the protein to be degraded and binds to Cullin via an adaptor protein. The E2 conjugating enzyme transfers multiple ubiquitin molecules to the substrate, targeting it for proteasomal degradation. HIV-1 Vif co-opts the Cullin5 E3 ubiquitin ligase, acting as a substrate receptor, targeting A3G for proteasomal degradation (see FIG. 1A). Both Cul2 and Cul5 bind their substrate receptors through the ElonginB-ElonginC adaptor proteins. Cellular substrate receptors have an additional interface that determines Cul2 or Cul5 selection, termed the Cul2 or Cul5 box, respectively.

Primate lentiviral Vif proteins do not have a Cul5 box although they specifically select Cul5. Some of the inventors and colleagues have previously identified a highly conserved HCCH zinc binding motif and demonstrated its requirement for Cul5 selection (see, e.g., Yu et al. (2004) Genes Dev 18, 2867-2872; Luo et al. (2005) Proc Natl Acad Sci USA 102, 11444-11449; Xiao et al. Virology 2006 Jun. 5; 349(2):290-9. Epub 2006 Mar. 13). Without wishing to be bound by any particular mechanism, it is suggested that this zinc binding domain acts to stabilize a putative helix with a hydrophobic face that is required for Cul5 interaction (see FIG. 1B).

It would be desirable to identify an agent (e.g., a therapeutic agent) that can, e.g., inhibit HIV-1 Vif mediated A3G degradation in a cell, thereby blocking the degradation of the antiviral agent, A3G, and thus inhibiting HIV-1 infectivity.

DESCRIPTION OF THE DRAWINGS

FIGS. 1A-1D show that intracellular zinc chelation inhibits Vif interaction with Cul5. FIG. 1A shows that HIV Vif acts as a substrate receptor, assembling with Cul5, ElonginB, and ElonginC to form an E3 ubiquitin ligase. The Cul5-Vif E3 ubiquitin ligase binds A3G and brings it in close proximity with the E2 ubiquitin conjugating enzyme. Polyubiquitinated A3G is recognized by the proteasome and subsequently degraded. FIG. 1B shows a model of the zinc stabilized motif in HIV Vif that is required for Cul5-Vif interaction. FIG. 1C shows that increasing concentrations of TPEN decrease Cul5 interaction in a dose dependent manner. 293T cells were transfected with Vif-HA expression vectors as previously described and treated with the indicated amounts of TPEN. Vif-HA was immunoprecipitated and eluted materials were then analyzed by SDS-PAGE and immunoblotting for Cul5, Vif-HA, ElonginB, and ElonginC. FIG. 1D shows that TPEN treatment has no effect on transcription and translation of Cul5 and Vif. 293T cells were transfected with Vif-HA and treated with the indicated amounts of TPEN. Cell lysates were harvested and analyzed by SDS-PAGE and immunoblotting for Cul5 and Vif-HA.

FIGS. 2A-2C show that zinc is required for Cul5 selection by diverse primate lentiviral Vif proteins. FIG. 2A shows an alignment illustrating divergence in the spacing of SIVagm and SIVsyk zinc binding motifs. Hydrophobic residues are represented by a Phi ($\Phi$). FIG. 2B shows that SIVagm and SIVsyk require zinc for Cul5 selection despite divergence in spacing from the zinc binding consensus of HIV Vif. 293T cells were transfected with the indicated SIV Vif expression vectors and treated with 4 µM TPEN. Cell lysates were immunoprecipitated and analyzed by SDS-PAGE followed immunoblotting for Cul5, HA, ElonginB, and ElonginC. FIG. 2C shows that the cellular substrate receptor SOCS-3 does not require zinc for Cul5 selection. 293T cells were transfected with SOCS-3-HA and treated with 4 µM TPEN. Cell lysates were immunoprecipitated and analyzed by SDS-PAGE and immunoblotting.

FIG. 3A shows that PEN treatment inhibits A3G degradation. 293T cells were transfected with the indicated plasmids in the presence of 4 µM TPEN or control vehicle. Cell lysates were analyzed for A3G degradation by SDS-PAGE followed by immunoblotting for A3G-HA, Vif-myc, and ribosomal p19 as a loading control. FIG. 3B shows that zinc chelation has no effect on Vif-A3G interaction. 293T cells were transfected with the indicated plasmids and treated with 411M TPEN or control vehicle. Vif-HA was immunoprecipitated from prepared lysates. Lysates were analyzed by SDS-PAGE followed by immunoblotting for Vif-HA and A3G-myc. FIG. 3C shows that TPEN treatment increases virion incorporation of A3G. Cells were infected with WT or ΔVif NL4-3 virus in the presence of A3G-myc and treated with 4 µM TPEN or DMSO. Cells were harvested and virus was isolated from the supernatant by ultracentrifugation and analyzed by SDS PAGE and immunoblotting against Vif, myc, and p24. FIG. 3D shows that TPEN does not interfere with Rbx function. Adenovirus E4orf6 mediated p53 degradation is not affected by 4 µM TPEN. 293T cells were transfected with p53 and E4orf6-myc expression vectors in the presence of 4 µM TPEN or control vehicle. Cells were harvested and analyzed for p53 degradation by SDS-PAGE followed by immunoblotting for p53, E4orf6-myc, and ribosomal p19 as a loading control.

DETAILED DESCRIPTION

Figures 3A, 3B:
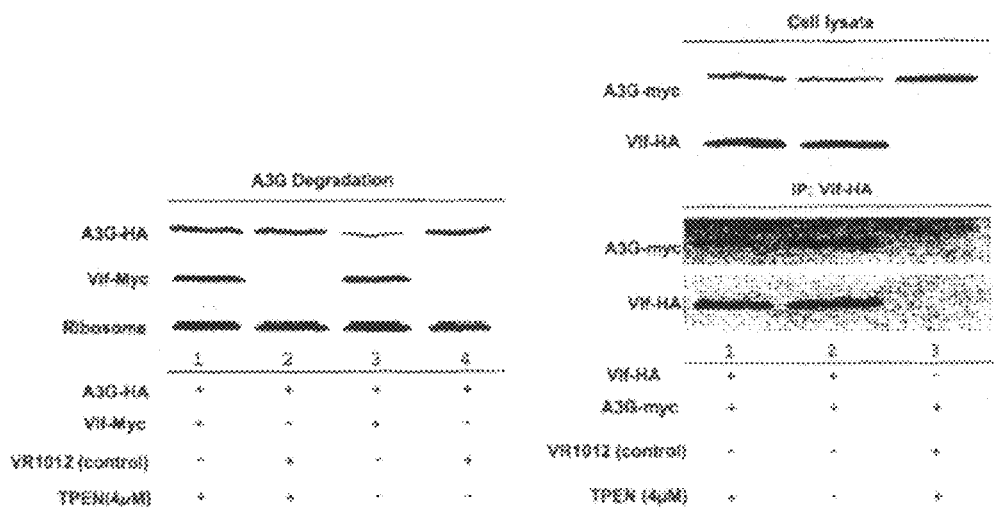
FIGS. 3A-3D show that intracellular zinc chelation inhibits Vif mediated A3G degradation.

This invention relates, e.g., to a method for inhibiting the infectivity of a lentivirus (e.g., a lentivirus which expresses Vif), such as, e.g., SIV, SHIV and/or HIV, comprising contacting a cell that is producing the virus with an antiviral-effective amount of a membrane-permeable Zinc (Zn) chelator (e.g., N,N,N',N'-Tetrakis-(2-pyridylmethyl) ethylenediamine (TPEN)), wherein the antiviral-effective amount of the Zn chelator does not substantially inhibit proteins in the cell which contain Zn binding motifs other than Vif.

The inventors show herein, using TPEN, that zinc is required for HIV-1 Vif mediated A3G degradation in cell culture (cell culture studies are sometimes referred to herein as "in vivo" studies). Treatment with a membrane-permeable zinc chelator resulted in increased A3G stability, allowing it to be packaged within the virion, where it drastically inhibited virus infectivity. Unexpectedly, the TPEN concentrations required to inhibit virus infectivity did not affect the function of a number of cellular zinc binding proteins. Therefore, it would be expected that treatment of a subject who is infected with a lentivirus with a membrane permeable zinc chelator will elicit few, if any, toxic side effects resulting from inhibition of cellular zinc binding proteins. This is one advantage of a method of the invention.

Many current anti-HIV drugs target the function of viral proteins such as reverse transcriptase and protease. The high mutation rate of the HIV virus and noncompliance with treatment regimens has resulted in an increased incidence of antiviral drug resistance. Another advantage of a method of the present invention is that, because it does not target conventional lentiviral proteins (e.g., reverse transcriptase, protease, integrase, proteins that modulate the entry of the virus into a cell, proteins that modulate assembly/maturation of the virus, or the like), a method of the invention functions even if the lentivirus is resistant to agents which target such proteins. Similarly, a method of the invention can inhibit the infectivity of a variety of other types of mutant or variant lentiviruses.

One aspect of the invention is a method for inhibiting infectivity of a lentivirus (e.g., a lentivirus which expresses a Viral infectivity factor (Vif) protein), such as the simian immunodeficiency lentiviruses SIV, SHIV and/or HIV, comprising contacting a cell which is producing the virus with an antiviral-effective amount of a membrane-permeable Zinc (Zn) chelator (e.g., TPEN), wherein the antiviral-effective amount of the Zn chelator does not substantially inhibit proteins in the cell which contain Zn-binding motifs other than Vif. For example, the antiviral-effective amount of TPEN can be effectively between about 4 and about 12 µM, e.g., between about 4 and about 9 µM, or about 7 µM.

Another aspect of the invention is a method for inhibiting Vif protein activity in a cell, comprising contacting the protein with a Vif inhibitory-effective amount of a membrane-permeable Zn chelator, wherein the Vif inhibitory-effective amount of the Zn chelator does not substantially inhibit proteins in the cell which contain Zn-binding motifs other than Vif. For example, the Vif inhibitory-effective amount of TPEN can be effectively between about 4 and about 12 µM, e.g., between about 4 and about 9 µM, or about 7 µM.

A method of the invention may be carried out in cell culture or in a subject. For example, one aspect of the invention is a method for inhibiting infection of a host by a lentivirus (e.g., a lentivirus which expresses a Vif protein), such as SIV, SHIV and/or HIV (e.g., a method for treating lentiviral infection in a subject), comprising administering to the host/subject an antiviral effective amount of a membrane-permeable Zn chelator of the invention.

Another aspect of the invention is a method for identifying an agent that inhibits the infectivity of a lentivirus (e.g., a lentivirus which expresses a Vif protein comprising a Zn-binding motif as represented by SEQ ID NO:1), such as, e.g., SIV, SHIV and/or HIV, comprising (a) contacting a putative inhibitory agent with a peptide comprising the Vif Zn-binding motif represented by SEQ ID NO:1 ($Hx_{(2)}YFxCFx_{(4)}\Phi x_{(2)}A\Phi x_{(7-8)}Cx_{(3-5)}H$), in the presence of Cul5, under conditions that are effective for specific binding of the putative agent and the peptide; and (b) detecting whether the agent disrupts the binding of the peptide to Cul5, wherein an agent that significantly disrupts the binding is expected to inhibit lentiviral infectivity. A method of the invention in which putative inhibitory agents are so screened may be adapted to be a high throughput method.

Another aspect of the invention is a kit suitable for carrying out one of the methods of the invention. For example, a kit for inhibiting the infectivity of a lentivirus, e.g., a lentivirus which expresses a Vif protein (treating a lentiviral infection, e.g. in culture or in a subject) can comprise a (one or more) single dosage unit which comprises an antiviral-effective amount (and/or a Vif inhibitory-effective amount) of a membrane-permeable Zn chelator (e.g., TPEN), wherein the amount of the membrane-permeable Zn chelator is not sufficient to substantially inhibit proteins in the cell which contain Zn-binding motifs other than Vif. In one embodiment of the invention, the Zn chelator is TPEN, and the antiviral-effective amount of the TPEN in the single dosage unit results in a concentration (e.g. at a target tissue) of effectively between about 4 and about 12 µM, e.g., between about 4 and about 9 µM, or about 7 µM. The kit may optionally contain other components such as buffers, etc. suitable for carrying out the method, packaged together or separately in a container.

When the kit is for inhibiting the infectivity of the lentivirus in a subject (treating a lentiviral infection in a subject), the membrane-permeable Zn chelator may be in the form of a pharmaceutical composition (e.g., it comprises a pharmaceutically acceptable carrier). In one embodiment of the invention, the Zn chelator in the kit is TPEN, and the antiviral-effective amount of the TPEN is effectively between about 0.5 mg/kg and about 30 mg/kg, e.g. between about 0.5 mg/kg and about 10 mg/kg. The dosage units in the kit are expected to be between 5 mg and 3 g.

Another embodiment of the invention is a kit for identifying an agent that acts as an inhibitor of infectivity of a lentivirus (e.g., a lentivirus which expresses a Vif protein comprising a Zn-binding motif as represented by SEQ ID NO:1), such as, e.g., SIV, SHIV and/or HIV. The kit can comprise: (a) a peptide comprising a Zn-binding motif as represented by SEQ ID NO:1; (b) Cul5; and (c) one or more reagents for detecting whether the peptide binds to the Cul5, wherein, optionally, (a), (b) and/or (c) are packaged in a container or other packaging material.

Another aspect of the invention is a pharmaceutical composition that comprises an amount of a membrane-permeable Zn chelator (e.g., TPEN) that is effective to inhibit infection by a lentivirus (e.g., a Vif-expressing lentivirus), such as, e.g., SW, SHIV or HIV, but that does not substantially inhibit proteins in the cell which contain Zn-binding motifs other than Vif, and a pharmaceutically acceptable carrier. The effective amount of the Zn chelator can be, e.g., an amount that results in a concentration at a target tissue of effectively between about 4 and about 12 µM, e.g., between about 4 and about 9 µM, or about 7 µM. For example, the pharmaceutical composition can comprise between about 0.5 mg/kg and about 10 mg/kg. The dosage units are expected to range between 5 mg and 3 g.

Another aspect of the invention is a complex comprising a membrane-permeable zinc chelator and a Vif protein. Such a complex can exist either in the context of a cell culture or in a subject. The complex would be expected to be an intermediate following contacting a cell that is infected with a suitable lentivirus with a membrane-permeable zinc chelator of the invention, or following treatment of a subject infected with a suitable lentivirus with a membrane-permeable zinc chelator of the invention.

Other aspects of the invention are directed to the use of a membrane-permeable Zn chelator as a virucidal agent against a lentivirus (e.g., against SIV, SHIV and/or HIV). For example, one embodiment of the invention, which can be used to treat the blood supply, an organ or tissue destined for transplantation, etc., is a method for treating ex vivo a bodily fluid or tissue, comprising contacting the bodily fluid or tissue with a viral inhibitory effective amount of a membrane permeable Zn chelator. Another embodiment is a method for inhibiting contamination of an inanimate object, such as surgical or medical tubing or laboratory supplies, by a lentivirus (e.g., SIV, SHIV and/or HIV), comprising contacting the inanimate object with an antiviral effective amount of a membrane permeable Zn chelator. Another embodiment is a method for inhibiting (e.g., preventing) sexual transmission of infection by a lentivirus, comprising vaginal, rectal, oral, penile, or other topical, insertional or instillational treatment with an antiviral effective amount of a membrane-permeable Zn chelator of the invention.

As noted, one aspect of the invention is a method for inhibiting (e.g., decreasing or preventing) infectivity of a lentivirus (e.g., a lentivirus which expresses a Viral infectivity factor (Vif) protein), comprising contacting a cell which is producing the virus with an antiviral-effective amount of a membrane-permeable Zinc (Zn) chelator (e.g., TPEN), wherein the antiviral-effective amount of the Zn chelator does not substantially inhibit proteins in the cell which contain Zn-binding motifs other than lentivirus Vif.

As used herein, the singular forms of "a," "an," and "the" include plural referents unless the context clearly dictates otherwise. For example, "a" lentivirus, as used above, means one or more lentiviruses, which can be the same or different.

The lentivirus may be any of a variety of members of this genus of viruses; in one embodiment of the invention, the lentivirus contains a Vif protein that comprises a Zn-binding motif as discussed herein. The lentivirus may be, e.g., one that infects a mammal, such as a sheep, goat, horse, cow or primate, including human. Typical such viruses include, e.g., Vizna virus (which infects sheep); simian immunodeficiency virus (SIV), bovine immunodeficiency virus (BIV), chimeric simian/human immunodeficiency virus (SHIV), feline immunodeficiency virus (FIV) and human immunodeficiency virus (HIV). "HIV," as used herein, refers to both HIV-1 and HIV-2. Much of the discussion herein is directed to HIV or HIV-1; however, it is to be understood that other suitable lentiviruses are also included.

Without wishing to be bound by any particular mechanism, it is suggested that a zinc chelator may function to inhibit viral infectivity by the following type of mechanism: Treatment with a zinc chelator, such as TPEN, results in a defect in the ability of Vif to recruit Cul5 to the E3 ligase, which is thought to be an important component of the cellular ubiquitin protease machinery. The chelator targets a zinc stabilized domain in the HIV Vif protein that is required for the interaction with the cellular machinery required for Apobec3G degradation (or, for example, the degradation of other cellular Apobec3 proteins, such as A3C, A3DE or A3F). Removal of the zinc inhibits Vif function, allowing the virus to become sensitive to the antiviral activities of Apobec3G (or one of the other noted Apobec 3 proteins). Therefore, if a cell that is producing virus is treated with a suitable zinc chelator, virus that is being produced by the cell is inactivated and thus is unable (or exhibits a reduced capacity) to carry out future rounds of infection. In this manner, infectivity of the virus is inhibited.

The invention is not limited to the mechanism suggested above. The invention includes the inhibition of infectivity of a lentivirus by a membrane-permeable zinc chelator, and/or by TPEN, regardless of the mechanism by which the agent inhibits the infectivity. One aspect of the invention is a method for inhibiting the infectivity of a lentivirus, comprising contact a cell which is producing the virus with an antiviral-effective amount of TPEN, wherein the antiviral-effective amount of TPEN is effectively between about 4 and about 12 µM, e.g., effectively between about 4 and about 9 µM, or effectively about 7 µM. When treating a subject, the antiviral-effective amount of TPEN can be between about 0.1 or 0.5 mg/kg and about 30 mg/kg, e.g. between about 0.5 mg/kg and about 10 mg/kg.

In one embodiment of the invention, the Zn-stabilized domain/motif of the Vif protein is $H_{-x2}$-YF-$_x$-CF-$_{x4}$-$\Phi_{-2}$-A$\Phi$-$_{x7-8}$-C-$_{x3-5}$-H (SEQ ID NO:1), wherein $\Phi$ is a hydrophobic amino acid, such as I, L or V. The identification of this consensus sequence is described in Example II and in FIG. 2A. In other embodiments, the Zn-stabilized motif is about 90%, 95%, 98% or 99% identical with SEQ ID NO:1. In other embodiments, an unrelated Zn-binding motif may substitute for the sequence represented by SEQ ID NO:1.

An "antiviral-effective" amount of an inhibitor includes an amount that is sufficient to reduce the infectivity of the virus by a detectable (measurable) amount. For example, when used in tissue culture, the antiviral effective amount of TPEN can be effectively between about 4 and about 12 µM, e.g., between about 4 and about 9 µM, or about 7 µM in the culture medium. Effective concentrations of membrane-permeable zinc chelators other than TPEN can be readily determined by a skilled worker, based on the findings herein with regard to TPEN and by use of routine optimization procedures.

The term "about" as used herein means plus or minus 10%. Thus, "about" 7 includes 6 or 8. Ranges herein include the endpoints. Thus, a range of between 4 and 12 µM includes both 4 µM and 12 µM. Furthermore, where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

With regard to "antiviral-effective" dosages in a subject, the amount can be determined routinely by a skilled worker, for example based on the findings herein that treatment with TPEN is effective with an $IC^{50}$ of about 1.79 µM, and with relation to the values identified herein as being effective for viral inhibition in cell culture. To produce an antiviral-effective concentration in a target tissue or organ (such as blood, or lymphoid tissues, such as lymph nodes, spleen, thymus and the gut, or cells of lymphoid origin in the brain) in a subject that is being treated, an amount of TPEN is administered so that the local concentration in the target tissue is at least about 1.79 µM, 2 times that value, 3 times that value, 4 times that value, 5 times that value, etc. Based on these values, it is expected that on average between about 0.1 or 0.5 mg/kg and about 30 mg/kg would be needed, e.g. between about 0.5 mg/kg and about 10 mg/kg.

As used herein, a phrase such as "the antiviral effective amount of TPEN can be effectively between about 4 and about 12 µM" means that the amount is between about 4 and about 12 µM in tissue culture medium when the TPEN is added in cell culture, and that this amount is achieved in a target tissue or organ when the TPEN is administered to a subject.

In general, the antiviral effective amount of a membrane permeable Zn chelator of the invention is an amount which does not substantially inhibit proteins in a cell that contain Zn-binding motifs other than Vif. By "substantially," as used herein in this context, is meant an amount that inhibits, e.g., less than about 75%, 50%, 25%, 10%, 5%, 2% or 1% of the activity of such proteins. Generally, less than about 5% of the activity of such proteins is inhibited.

A further discussion of dosages for treatment of a subject and methods for optimizing the doses is presented elsewhere herein.

Another aspect of the invention is a method for inhibiting Vif protein activity in a cell, comprising contacting the protein with an inhibitory-effective amount of a membrane-permeable Zn chelator, wherein the inhibitory-effective amount of the Zn chelator does not substantially inhibit proteins in the cell which contain Zn-binding motifs other than lentivirus Vif. An "inhibitory-effective amount" is an amount that results in a detectable (e.g., measurable) amount of inhibition of an activity of Vif, such as its ability to target and degrade A3G in a cell infected by a lentivirus.

Any of a variety of suitable membrane-permeable Zn chelators can be used in a method of the invention. A variety of Zn chelators will be evident to a skilled worker. These chelators are suitable, provided that the molecules are permeable to a cell membrane.

Chelators have been characterized that preferentially chelate zinc, or that are relatively specific for zinc in addition to one or more other metal ions, such as copper. A "chelating agent," as used herein, is a compound having multiple sites (two, three, four or more) which can simultaneously bind to a metal ion or metal ions such as, for example, zinc, lead, cobalt, iron or copper ions. The binding sites typically comprise oxygen, nitrogen, sulfur or phosphorus. For example, salts of EDTA (ethylenediaminetetraacetic acid) can form at least four to six bonds with a metal ion or metal ions via the oxygen atoms of four acetic acid moieties ($—CH_2C(O)^O$) and the nitrogen atoms of ethylenediamine moieties ($>N—CH_2—CH_2—N<$) of EDTA. It is understood that a chelating agent also includes a polymer which has multiple binding sites to a metal or metal ions. Preferably, a chelating agent of the invention is non-toxic and does not cause unacceptable side effects at the dosages being administered. As a chelating agent of the invention, a zinc-chelating agent is preferable. A "zinc-chelating agent" refers to a chelating agent which can bind to a zinc ion or zinc ions.

Examples of chelating agents (not all of which are membrane permeable) include, e.g., penicillamine, trientine, N,N'-diethyldithiocarbamate (DDC), 2,3,2'-tetraamine (2,3,2'-tet), neocuproine, N,N,N',N'-tetrakis(2-pyridylmethyl)ethylenediamine (TPEN), 1,10-phenanthroline (PHE), tetraethylenepentamine (TEPA), triethylene tetraamine and tris(2-carboxyethyl) phosphine (TCEP), bathophenanthroline disulfonic acid (BPADA), ethylene glycol (bis) aminoethyl ether tetra acetic acid (EGTA), nitrilotriacetic acid, TIRON™, N,N-bis(2-hydroxyethyl)glycine (bicine); O,O'-bis(2-aminophenyl ethylene glycol) ethylenediamine-N,N,N',N'-tetraacetic acid (BAPTA), trans-1,2-diamino cyclohexane-ethylenediamine-N,N,N',N'-tetraacetic acid (CyDTA), 1,3-diamino-2-hydroxy-propane-ethylenediamine-N,N,N',N'-tetraacetic acid (DPTA-OH), ethylene-diamine-N,N'-dipropionic acid dihydrochloride (EDDP), ethylenediamine-N,N'-bis(methylenephosphonic acid) hemihydrate (EDDPO), ethylenediamine-N,N,N',N'-tetrakis(methylenephosphonic acid) (EDTPO), N,N'-bis(2-hydroxybenzyl)ethylene diamine-N,N'-diacetic acid (HBED), 1,6-hexamethylenediamine-N,N,N',N'-tetraacetic acid (HDTA, or HEDTA), N-(2-hydroxyethyl)iminodiacetic acid (HIDA), iminodiacetic acid (IDA), 1,2-diaminopropane-N,N,N',N'-tetraacetic acid (methyl-EDTA), nitriltriacetic acid (NTA), nitrilotripropionic acid (NTP), nitrilotris (methylenephosphonic acid) trisodium salt (NTPO), triethylenetetramine-N,N,N',N'',N''-hexaacetic acid (TTHA), bathocuproine, bathophenanthroline, TETA, citric acid, salicylic acid, and malic acid, and analogues and derivatives, including hydrophobic derivatives and pharmaceutically acceptable salts thereof.

Suitable membrane-permeable Zn chelators include, e.g., TPEN; 1,10-O-phenanthroline; and diethyldithiocarbamate (DEDC). Chloroquinol is not an effective inhibitor in a method of the invention. Persons of skill in the art will be able to determine suitable compounds by routine testing using the methods described herein and known in the art.

Molecular biology methods used in aspects of the invention can be carried out using conventional procedures. See, e.g., discussions in Sambrook, et al. (current edition), *Molecular Cloning, a Laboratory Manual*, Cold Harbor Laboratory Press, Cold Spring Harbor, N.Y.; Ausubel et al. (current edition). *Current Protocols in Molecular Biology*, N.Y., John Wiley & Sons; Davis et al. (current edition), *Basic Methods in Molecular Biology*, Elseveir Sciences Publishing, Inc., New York; Hames et al. (current edition), *Nucleic Acid Hybridization*, IL Press; Dracopoli et al. (current edition) *Current Protocols in Human Genetics*, John Wiley & Sons, Inc.; Coligan et al. (current edition) *Current Protocols in Protein Science*, John Wiley & Sons, Inc.; Principles of Peptide Synthesis (Springer Laboratory), ed. (current edition), Bodanszky, Springer Verlag; and, Harlow et al. (current edition) Antibodies: A Laboratory Manual, Cold Spring Harbor Laboratory, Cold Spring Harbor, N.Y.

The order and numbering of the steps in the methods described herein are not meant to imply that the steps of any method herein must be performed in the order in which the steps are listed or in the order in which the steps are numbered. The steps of any method disclosed herein can be performed in any order which results in a functional method. Furthermore, the method may be performed with fewer than all of the steps, e.g., with just one step.

One aspect of the invention is a pharmaceutical composition comprising a membrane-permeable Zn chelator of the invention and a pharmaceutically acceptable carrier. In one embodiment, the chelator in the composition is in an amount which is effective for inhibiting infection by a lentivirus (e.g., a lentivirus which expresses Vif) and/or which is a Vif-inhibitory effective amount. In another embodiment, the Zn chelator is in a concentrated form, which can be diluted in a suitable carrier or excipient so that a suitable inhibitory amount can be administered to a subject.

Much of the discussion herein is directed to pharmaceutical compositions comprising lentiviral inhibitors which are membrane-permeable Zn chelators. However, it should be understood that other lentiviral inhibitors, which have been identified by a screening assay of the invention, are also included.

By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

A pharmaceutical composition of the invention can contain other pharmaceuticals, in conjunction with an inhibitor (e.g., a membrane-permeable Zn chelator) of the invention. Representative examples of these additional pharmaceuticals include antiviral compounds, virucides, immunomodulators, immunostimulants, antibiotics, absorption enhancers, and agents that inhibit contraception (such as nonoxynol-9). Exemplary antiviral compounds include AZT, ddI, ddC, gancyclovir, acyclovir, fluorinated dideoxynucleosides, non-nucleoside analog compounds, such as nevirapine (Shih et al. (1991), $PNAS$ 8, 9878-9882), TIBO derivatives, such as R82913 (White et al. (1991), $Antiviral$ $Res.$ 16, 257-266), BI-RJ-70 (Merigan (1991), $Am.$ $J.$ $Med.$ 90 (Supp.4A), 8S-17S), michellamines (Boyd et al., (1994) $J.$ $Med.$ $Chem.$ 37, 1740-1745), calanolides (Kashman et al. (1992), $J.$ $Med.$ $Chem.$ 35, 2735-2743), nonoxynol-9, gossypol and derivatives, gramicidin (Bourinbair et al., 1994, supra), and Ro 31-8959. Exemplary immunomodulators and immunostimulants include various interleukins, recombinant sCD4, cytokines (including α-interferon), antibody preparations, blood transfusions, and cell transfusions. Exemplary antibiotics include antifungal agents, antibacterial agents, and anti-$Pneumocystitis$ $carnii$ agents. Exemplary absorption enhancers include bile salts and other surfactants, saponins, cyclodextrins, and phospholipids (Davis, 1992, supra).

One skilled in the art will appreciate that the particular formulation will depend, in part, upon the particular inhibitor of the invention which is employed, and the chosen route of administration. Suitable routes of administration include, e.g., oral, aerosol, transdermal, topical, insertional, etc. Accordingly, there is a wide variety of suitable formulations of a composition of the present invention.

Formulations suitable for oral administration can consist of liquid solutions, such as an effective amount of the compound dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract (see, for example, Wallace et al. (1993), $Science$ 260, 912-915).

The inhibitors of the invention, alone or in combination with other antiviral compounds, can be made into aerosol formulations to be administered via inhalation. These aerosol formulations can be placed into pressurized acceptable propellants, such as dichlorodifluoromethane, propane, nitrogen and the like.

The inhibitors of the invention, alone or in combinations with other antiviral compounds or absorption modulators, can be made into suitable formulations for transdermal application and absorption (Wallace et al., 1993, supra). Transdermal electroporation or iontophoresis also can be used to promote and/or control the systemic delivery of the compounds and/or compositions of the present invention through the skin (e.g., see Theiss et al. (1991), $Meth.$ $Find.$ $Exp.$ $Clin.$ $Pharmacol.$ 13, 353-359).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; mouthwashes comprising the active ingredient in a suitable liquid carrier; or creams, emulsions, suspensions, solutions, gels, creams, pastes, foams, lubricants, sprays, suppositories, pessaries, tampons or the like.

Formulations for rectal administration can be presented as a suppository with a suitable base comprising, for example, cocoa butter or a salicylate. Formulations suitable for vaginal administration can be presented as pessaries, tampons, creams, gels, pastes, foams, or spray formulas containing, in addition to the active ingredient, carriers as are known in the art to be appropriate. Similarly, the active ingredient can be combined with a lubricant as a coating on a condom. Indeed, preferably, the active ingredient is applied to any contraceptive device, including, but not limited to, a condom, a diaphragm, a cervical cap, a vaginal ring, a dental dam, or a sponge.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Formulations comprising an inhibitor of the invention (such as a membrane-permeable Zn chelator) suitable for virucidal (e.g., HIV) sterilization of inanimate objects, such as medical supplies or equipment, laboratory equipment and supplies, instruments, devices, and the like, can, for example, be selected or adapted as appropriate, by one skilled in the art, from any of the aforementioned compositions or formulations.

Formulations suitable for ex vivo sterilization or removal of lentivirus from a sample, such as a bodily product (e.g., blood, blood products, sperm, fluids, cells, tissues or organs), or any other solution, suspension, emulsion, vaccine formulation, or any other material which can be administered to a patient in a medical procedure, can be selected or adapted as appropriate by one skilled in the art, from any of the aforementioned compositions or formulations.

One skilled in the art will appreciate that a suitable or appropriate formulation can be selected, adapted or developed based upon the particular application at hand.

Dosages for administration of an inhibitor (e.g., a membrane-permeable Zn chelator) of the invention can be in unit (single) dosage form, such as a tablet or capsule, or a specified volume of a liquid. The term "unit (or single) dosage form" as used herein refers to physically discrete units suitable as unitary dosages for human and animal subjects, each unit containing a predetermined quantity of a chelator/inhibitor of the invention, alone or in combination with other antiviral agents, calculated in an amount sufficient to produce the desired effect, e.g. in association with a pharmaceutically acceptable diluent, carrier, or vehicle. The unit dosage form can be, e.g., suitable for adding to a single cell culture (e.g., a single tissue culture vessel) or to a single subject (e.g., patient).

The specifications for the unit dosage forms of the present invention depend on the particular inhibitor (e.g. membrane-permeable Zn chelator) of the invention, or composition thereof, employed and the effect to be achieved, as well as the pharmacodynamics associated with the inhibitor in the host. In some embodiments, the dose administered is an "antiviral effective amount" or an amount necessary to achieve an "effective level" in the individual patient.

Since the "effective level" is used as the preferred endpoint for dosing, the actual dose and schedule can vary, depending upon individual differences in pharmacokinetics, drug distribution, and metabolism. The "effective level" can be defined, for example, as the blood or tissue level desired in the patient that corresponds to a concentration of the chelator/inhibitor which inhibits a lentivirus, such as HIV, in an assay known to predict for clinical antiviral activity of chemical compounds and biological agents. The "effective level" for agents of the present invention also can vary when the chelator/inhibitor of the invention, or composition thereof, is used in combination with AZT or other known antiviral compounds or combinations thereof.

One skilled in the art can easily determine the appropriate dose, schedule, and method of administration for the exact formulation of the composition being used, in order to achieve the desired "effective concentration" in the individual patient. One skilled in the art also can readily determine and use an appropriate indicator of the "effective concentration" of the compounds of the present invention by a direct (e.g., analytical chemical analysis) or indirect (e.g., with surrogate indicators such as p24 or RT) analysis of appropriate patient samples (e.g., blood and/or tissues).

For ex vivo uses, such as virucidal treatments of inanimate objects or materials, blood or blood products, or tissues, the amount of chelator/inhibitor, or composition thereof, to be employed is generally sufficient so that a detectable amount of, preferably most of, and most preferably all of, any virus or virus-producing cells present will be rendered noninfectious or will be prevented from infecting a cell. Similar considerations apply to in vivo applications, which are discussed more fully below. Therefore, the designation of an "effective amount" or an "antiviral effective amount" is used generally to describe the amount of a particular chelator/inhibitor of the invention, or composition thereof, required for at least a detectable amount of antiviral efficacy in any given application.

For in vivo uses (in a subject), the dose of a chelator/inhibitor of the invention, or composition thereof, administered to an animal, particularly a human, in the context of the present invention is generally sufficient to effect at least a detectable (measurable) prophylactic or therapeutic response in the individual over a reasonable time frame. In general, preferred times for administration are at the pre-entry/entry stage (e.g., pre- and post-fusogenic stages, such as gp41-mediated fusion). The exact amount of the dose will vary from subject to subject, depending on the species, age, weight and general condition of the subject, the severity or mechanism of any disorder being treated, the particular agent or vehicle used, its mode of administration and the like. The dose used to achieve a desired antiviral concentration in vivo (in a subject), (e.g., about 0.1 or 0.5 to about 30 mg/kg, or about 0.5 to about 10 mg/kg, e.g., given in one or more doses at intervals of 0, 2, 4, 6, 8, 12 etc. hours.) will be determined by the potency of the particular chelator/inhibitor employed, the severity of the disease state of infected individuals, as well as, in the case of systemic administration, the body weight and age of the infected individual. The size of the dose also will be determined by the existence of any adverse side effects that may accompany the particular inhibitory agent of the invention, or composition thereof, employed. It is generally desirable, whenever possible, to keep adverse side effects to a minimum.

Initial dosage ranges can be selected to achieve an inhibitory concentration in target tissues that is similar to inhibitory concentrations determined in cell culture experiments. The dosage should not be so large as to cause adverse side effects, such as unwanted cross-reactions, anaphylactic reactions, and the like. The dosage can be adjusted for each individual in the event of any contraindications and can be readily ascertained without resort to undue experimentation. In any event, the effectiveness of treatment can be determined by monitoring the viral load of a patient infected with the immunodeficiency virus. The viral load will decrease following administration of an effective agent. In one embodiment, the level of CD4+ T-cells is also monitored in the patient.

Suitable subjects that can be treated by a method of the invention include any animal that can be infected by a lentivirus, and in which treatment with an inhibitor (e.g. a membrane-permeable Zn chelator) of the invention can inhibit the infectivity of the virus. Suitable subjects include, e.g., vertebrate animals, e.g. mammals (including pets, farm animals, research animals, and primates, including humans).

Another aspect of the invention is a method for identifying an agent (e.g. screening putative agents for one or more that elicits the desired activity) that inhibits the infectivity of a lentivirus (e.g., a lentivirus which expresses a Vif protein, such as one that comprises a Zn-binding motif as represented by SEQ ID NO: 1). Typical such lentiviruses include, e.g., SIV, SHIV and/or HIV. The method takes advantage of the demonstration in the present application that the Zn-binding motif represented by SEQ ID NO: 1 appears to be unique to primate lentiviruses (including the human virus, HIV). An agent that binds specifically and sufficiently avidly to this motif would be expected to inhibit infectivity of a lentivirus that expresses a Vif protein comprising the motif. Furthermore, because the motif is not found in other cellular proteins, such an agent would not be expected to interfere with the function of cellular proteins and thus would be expected to elicit few, if any, side effects as a result of the binding.

The method comprises: (a) contacting a putative inhibitory agent with a peptide comprising the Zn-binding motif represented by SEQ ID NO:1 ($Hx_{(2)}YFxCFx_{(4)}\Phi x_{(2)}A\Phi x_{(7-8)}Cx_{(3-5)}H$), under conditions that are effective for specific binding of the putative agent and the peptide; and (b) detecting whether the agent has bound specifically to the peptide, at a sufficiently high affinity to inhibit activity of Vif. Any of a variety of conventional procedures can be used to implement such an assay. For example, the peptide may be detectably labeled, either directly or indirectly; the peptide may be bound to a surface, etc. The determination of whether the binding is at a sufficiently high affinity to inhibit Vif can be carried out in a second step, if desired.

Another method for identifying an agent that inhibits the infectivity of a such a lentivirus comprises identifying an agent that disrupts an interaction between Vif and Cul5 which is mediated by the Zn-binding motif as represented by SEQ ID NO:1 (but that does not disrupt the interaction between, e.g., Clu5 and E4orf6 or between Cul5 and SOCS3). The method can comprise, e.g.: (a) contacting a putative inhibitory agent with a peptide comprising the Zn-binding motif represented by SEQ ID NO:1 ($HX_{(2)}YFxCFX_{(4)}\Phi x_{(2)}A\Phi x_{(7-8)}Cx_{(3-5)}H$), in the presence of Cul5, under conditions that are effective for specific binding of the putative agent and the peptide; and (b) detecting whether the agent disrupts the binding of the Vif to the Cul5, wherein an agent that significantly disrupts the binding is expected to inhibit lentiviral infectivity. By "significantly disruption" is meant a statistically significant degree of disruption.

Any of a variety of conventional procedures can be used to carry out such an assay. For example, the assay can be carried out using cells that express Vif and Cul5. Suitable cells (e.g., bacterial cells, yeast cells, or mammalian cells whose membranes are similar or identical to cells which are infected by HIV) can be engineered to express Vif and Cul5, each labeled with one or a pair of markers that are compatible in a FRET assay, such as either CFP and YFP, or Cy3 and Cy5, respectively. A FRET (Fluorescence Resonance Energy Transfer) biosensor assay can then be used to analyze whether the two proteins have bound. This assay works by assessing the distance between two appropriately labeled proteins, based on transfer of fluorescence resonance energy. When bound together, the fluorescence would measure one value; but when an inhibitor disrupts the binding, the fluorescence would decrease to that of the individual dye. In addition to testing the effectiveness of a putative inhibitory agent, the assay will also determine whether a putative agent is able to permeate a cell membrane. Methods for carrying out such an assay are conventional and well-known in the art. Suitable controls, such as examining the binding, in the presence of the putative agent, between Cul5 and E4orf6 or between Cul5 and SOCS3, will be evident to the skilled worker.

In a screening method of the invention, peptides having specific Zn-binding motifs, such as those represented by SEQ ID NO:2 (HIV-1 VIF -HLYYFDCFSD-SAIRKALLGHIVSPRCEYQAGH), SEQ ID NO:3 (TAN-TAN1 -HCHYFPCFTDRAIQQAIRGESFLW-CTYKEGH), and SEQ ID NO:4 (SYK-SYK173 -HNFYFPCFTARAVN-QAVRGELLTSHCWTPH), can also be used.

A screening method of the invention may be adapted to be a high throughput format, using automated (e.g. robotic) systems, which allow many measurements to be carried out and/or analyzed simultaneously. Furthermore, the methods can be miniaturized.

Any of a variety of types of putative inhibitory agents can be screened by a method of the invention. For example, one can screen small molecules, including naturally occurring or chemically synthesized molecules, e.g. derived by combinatorial chemistry, including, e.g., variants of TPEN or of other membrane-permeable Zn chelators; polypeptides, peptides or peptidomimetics, e.g. derived from random peptide libraries, that bind to the Zn-binding motif and thereby interfere with its activity (but that cannot substitute for Vif); antibodies specific for the motif (including monoclonal or polyclonal antibodies, active fragments of antibodies, aptamers, human or humanized antibodies, etc.); and other types of molecules that will be evident to a skilled worker. Methods for generating such putative inhibitors are conventional and well-known in the art.

"Small molecules," sometimes referred to herein as "compounds," can be generated as follows: Such small molecules may be isolated from natural sources or developed synthetically, e.g., by combinatorial chemistry. In general, such molecules are identified from large libraries of natural products or synthetic (or semi-synthetic) extracts or chemical libraries according to methods known in the art. Those skilled in the field of drug discovery and development, for example, will understand that the precise source of test extracts or compounds is not critical to the methods of the invention. Accordingly, virtually any number of chemical extracts or compounds can be used in the methods described herein. Examples of such extracts or compounds include, but are not limited to, plant-, fungal-, prokaryotic- or animal-based extracts, fermentation broths, and synthetic compounds, as well as modification of existing compounds. In particular, it may be desirable to start with TPEN and to modify it to optimize its inhibitory properties and/or to reduce its toxic properties. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon Associates (Merrimack, N.H.) and Aldrich Chemical (Milwaukee, Wis.).

Alternatively, libraries of natural compounds in the form of bacterial, fungal, plant, and animal extracts are commercially available from a number of sources, e.g., Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

Any combination of the materials useful in the disclosed methods can be packaged together as a kit for performing any of the disclosed methods. If desired, the reagents are packaged in single use form, suitable for carrying one set of treatments or drug screens.

In one embodiment of the invention, a kit for inhibiting the infectivity of a lentivirus (e.g., a lentivirus which expresses a Vif protein) can comprise a single dosage unit which comprises an antiviral-effective amount (and/or a Vif inhibitory-effective amount) of a membrane-permeable Zn chelator (e.g., TPEN), wherein the amount of the membrane-permeable Zn chelator is not sufficient to substantially inhibit proteins in the cell which contain Zn-binding motifs other than Vif. The Vif inhibitor may optionally be packaged in a container. The kit may be designed for inhibiting the viral infectivity in cell culture or in a subject. In one embodiment, in which the kit is for inhibiting the infectivity of the lentivirus in a subject, the membrane-permeable Zn chelator may be in the form of a pharmaceutical composition (e.g., it comprises a pharmaceutically acceptable carrier). In another example, a kit for identifying an agent that acts as an inhibitor of levtivirus infectivity, can comprise (a) a peptide comprising a Zn-binding motif as represented by SEQ ID NO:1; and, optionally, (b) one or more reagents for detecting specific binding of the peptide to a candidate inhibitory agent, and/or (c) one or more reagents for measuring the binding affinity between a putative agent and the peptide. Optionally, (a), (b) and/or (c) are packaged in a container or other packaging material.

Kits may supply reagents in pre-measured amounts so as to simplify the performance of the subject methods. Optionally, kits of the invention comprise instructions for performing the method. Other optional elements of a kit of the invention include suitable buffers, packaging materials, etc. The kits of the invention may further comprise additional reagents that are necessary for performing the subject methods. The reagents of the kit may be in containers in which they are stable, e.g., in lyophilized form or as stabilized liquids.

In the foregoing and in the following example, all temperatures are set forth in uncorrected degrees Celsius; and, unless otherwise indicated, all parts and percentages are by weight.

EXAMPLES

Example I

Materials and Methods

A. Plasmid Construction

Plasmids NL4-3, NL4-3ΔVif, pHIV-IVif-HA, pHIV-1Vif-cmyc, SIVagmTanVif, SIVsyk173Vif phApo3G-HA, and phApo3G-myc have been described (Yu et al. (2003) (supra); Luo et al. (2005) (supra); Liu et al. (2004) *J. Virol* 78, 2072-2081). VR1012 is the parental vector of pHIV-1 Vif and was used as a control vector in the absence of Vif. The adenovirus E4orf6 and human p53 expression vectors (pCMV6.9 and pC53SN3 respectively) were gifts from Gary Ketner (Boyer et al. (2000) *J Biol Chem* 275, 14969-14978). HA-tagged SOCS3 was a generous gift from Nicholas A. Cacalano (UCLA).

B. Cell Culture, Transfection, MAGI Assay, and Antibodies 293T and MAGI-CCR5 cells (Chackerian et al. (1997) *J Virol* 71, 3932-3939) were maintained and transfected or infected as previously described (Yu et al. (2003) (supra)). The MAGI assay was performed as described previously and the antibodies used in this study have been described: anti-HA antibody-agarose conjugate, anti-myc antibody-agarose conjugate, anti-Vif, anti-Elongin B, anti-Elongin C, anti-Myc, anti-HA, and anti-human ribosomal P antigens (Yu et al. (2003) (supra)). The anti-p53 mouse mAb was obtained from Oncogene Research Products (Cat. #OP03).

C. In Vivo (Cell Culture) Zinc Chelation

Medium was removed 12 h prior to harvesting cells and replaced with either fresh medium alone or medium containing the indicated concentration of TPEN (Sigma). After a 12-h incubation, the cells were harvested for immunoprecipitation and immunoblot analysis, or the medium was collected for MAGI assay.

D. Immunoprecipitation and Immunoblot Analysis

Transfected 293T cells were harvested, washed twice with cold PBS, and lysed in lysis buffer (50 mM Tris, pH 7.5, with 150 mM NaCl, 1% Triton X-100, and complete protease inhibitor cocktail tablets) at 4° C. for 1 h, then centrifuged at 10,000×g for 30 min. For myc-tag immunoprecipitation, precleared cell lysates were mixed with anti-myc antibody (Upstate) and incubated with protein G at 4° C. for 3 h. For HA tag immunoprecipitation, precleared cell lysates were mixed with anti-HA antibody-conjugated agarose beads (Roche) and incubated at 4° C. for 3 h. Samples were then washed three times with washing buffer (20 mM Tris, pH 7.5, with 100 mM NaCl, 0.1 mM EDTA, and 0.05% Tween-20). The beads were eluted with elution buffer (0.1 M glycine-HCl, pH 2.0) or 2× loading buffer. The eluted materials were then analyzed by SDS-PAGE and immunoblotting as previously described (Yu et al. (2003) (supra)).

Example II

Assessment of the Requirement for Zinc for the Interaction of HIV-1 Vif with the Cul E3 Ligase and Degradation of A3G in Cell Culture (In Vivo)

We employed the membrane permeable zinc chelator TPEN, and identified a TPEN concentration that would interfere with Vif selection of Cul5 while leaving the function of cellular zinc binding proteins such as A3G and Rbx, a zinc dependent component of the E3 ligase, intact. Specifically interfering with the Vif-Cul5 interaction allows HIV-1 to efficiently package A3G, allowing HIV to become sensitive to the activities of the antiviral protein even in the presence of Vif.

When Vif-expressing 293T cells were treated with increasing concentrations of TPEN, Cul5-Vif interaction decreased in a dose dependent manner while interaction with ElonginB and ElonginC remained constant (FIG. 1C). From these data, we determined TPEN to have an $IC^{50}$ of 1.79 μM. TPEN treatment did not have any effect on cellular Cul5 protein levels, suggesting that this effect was due to the requirement of zinc for Vif-Cul5 interaction, and not due to a global effect on translation, (FIG. 1D). This data demonstrate the requirement of zinc in vivo for the recruitment of Cul5 by HIV-1 Vif.

In order to identify a conserved consensus sequence in the HCCH motif in Vif, we aligned the sequences of primate lentiviral Vif proteins. The resulting alignment, as illustrated in FIG. 2A, shows that the consensus motif-$H_{x2}$-YF-$_x$-CF-$_{x4}$-$\Phi_{x2}$-A$\Phi_{x7-8}$-C-$_{x3-5}$-H (SEQ ID NO: 1)—is highly conserved in primate lentiviral Vif proteins. The spacing between the first His and the first Cys is invariably five amino acids. The spacing between the first and second Cys is also highly conserved, with the exception of SIVagm, which has 17 rather than 18 amino acids between these positions. In addition, while most HIV/SIV Vif proteins have five amino acids between the second Cys and the second His, SIVsyk Vif has only three amino acids. We have also found that exchanging Cys for His and vice versa in this motif disrupts Vif function and interaction with Cul5; and that maintenance of both conserved residues and spacing within the consensus sequence represented by SEQ ID NO:1 is required for Cul5 selection and subsequent A3G degradation.

In order to verify that zinc is required for Cul5 selection and E3 ligase complex formation in Vif proteins with divergent zinc binding motif spacing, we again employed TPEN. 293T cells were transfected with SIVagm or SIVsyk Vif expression vectors and treated with 411M TPEN or control vehicle DMSO (FIG. 2B). Upon immunoprecipitation of Vif, we detected equal amounts of ElonginB and ElonginC, independent of TPEN treatment; however, for all immunoprecipitated Vif proteins we observed a marked decrease in Cul5 co-immunoprecipitation in TPEN treated cells when compared to vehicle treated controls (FIG. 2B). These data taken together suggest that the HCCH motif in primate lentiviral Vif proteins represents a zinc binding region that is required for interaction with Cul5 in vivo, irrespective of minor spacing divergence.

While few well characterized cellular functions of the Cul5 E3 ligases are known, a number of Cul5 specific substrate receptors have been identified (see, e.g., Kamura et al. (1998) *Genes Dev* 12, 3872-3881; Kamura et al. (2004) *Genes Dev* 18, 3055-3065; Brower et al. (2002) *Proc Natl Acad Sci USA* 99, 10353-10358; Kamura et al. (2001) *J Biol Chem* 276, 29748-29753). In order to determine whether zinc mediated Cul5 recruitment was unique to primate lentiviral Vif proteins, we assessed the effect of TPEN on the cellular Cul5-SOCS-3 E3 ligase. Upon immunoprecipitation of SOCS-3 in the presence of 41M TPEN or control DMSO, we detected equal interaction with Cul5, suggesting that zinc is not required for interaction of the cellular substrate receptor SOCS-3 with Cul5 (FIG. 2C). In addition, we observed similar results when we evaluated the effect of TPEN on the interaction of the Adenovirus protein E4orf6 with Cul5 (data not shown). These data demonstrate that the HCCH zinc binding motif as represented by SEQ ID NO:1 is unique to the Vif-Cul5 interaction. The ability of E4orf6 to efficiently degrade p53 in the presence of TPEN addresses the effect of zinc chelation on Rbx. Without wishing to be bound by any particular mechanism, it is suggested that Vif binds zinc weakly relative to cellular proteins such as A3G and Rbx at the concentrations used in our studies. Thus, it appears that the interaction between Vif and Cul5 E3 ligase is disrupted using TPEN concentrations that do not affect stronger zinc binding cellular proteins such a A3G and Rbx.

Example III

Figures 3C, 3D:
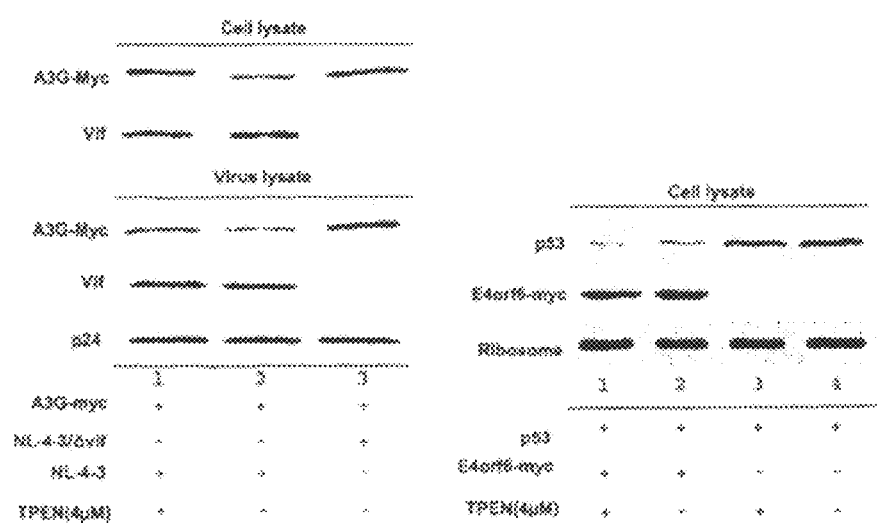

Determination of the Functional Relevance of the Zinc Requirement and Assessment that A3G Retained Antiviral Function in the Presence of 7 µM TPEN In order to determine the functional relevance of the sinc binding motif in HIV-1, we studied the effect of zinc chelation on A3G degradation. In the absence of TPEN, HIV-1 Vif induces the degradation of A3G; however, upon addition of TPEN, A3G degradation was abolished (FIG. 3A, compare lane 1 and lane 3). TPEN had no effect on A3G expression or stability in the absence of HIV-1 Vif (FIG. 3A, lane 2). Without wishing to be bound by any particular mechanism, it is suggested that the observed effect of zinc chelation on A3G degradation was presumably due to the loss of Cul5 as zinc chelation had no effect on Vif-A3G interaction (FIG. 3B). In the absence of TPEN and in the presence of Vif, A3G levels were reduced in both the cell and virion, as would be expected (FIG. 3C, compare lane 2 and 3). Upon addition of TPEN, however, cellular A3G protein levels were increased, enhancing incorporation into virions even in the presence of Vif (FIG. 3C, lanes 1 and 3). These data demonstrate the requirement of zinc for Vif degradation of A3G and subsequent exclusion from the virus.

Rbx is required for recruitment of the E2 ubiquitin conjugating enzyme and neddylation of Cullin, two functions that are required for E3 activation and subsequent activity. Since zinc is required for Rbx function, we wanted to confirm that the effects of TPEN treatment that we had observed were not due to disruption of Rbx function. To evaluate the effect of TPEN on Rbx function, we utilized one of the only other well characterized Cul5 E3 ligase systems. The adenovirus protein E4orf6 acts as a Cul5 substrate receptor, functioning to degrade cellular p53. In the absence of E4orf6, p53 levels are stable (FIG. 3D, lanes 3 and 4). However in the presence of the viral substrate receptor, p53 levels decline (FIG. 3D, lane 2). p53 levels also declined in the presence of 4RM PEN, indicating that the effect of zinc chelation on A3G degradation is not due to a defect in Rbx function (FIG. 3D, lane 1).

Figure 4:
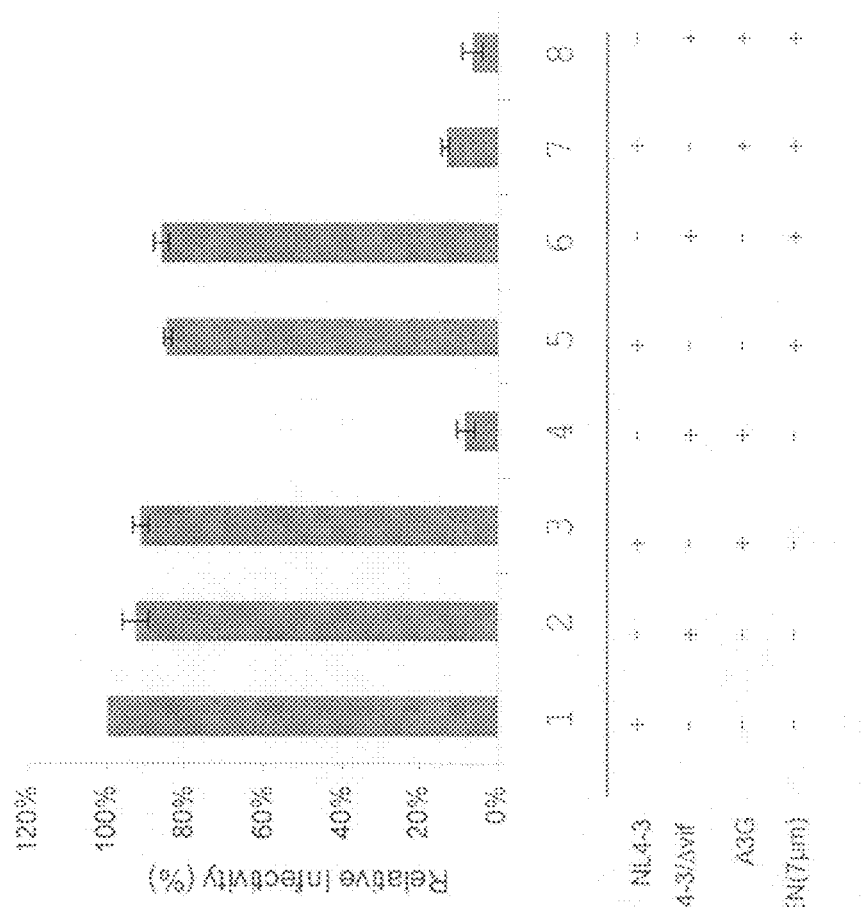
FIG. 4 shows that Zinc chelation drastically reduces virus infectivity in the presence of MG. MAGI cells were infected with wild-type or Vif deficient NL4-3 produced in the absence or presence of A3G and 7gM TPEN as indicated. Relative infectivity was calculated by setting wild type virus infectivity to 100% (lane 1).

In order to assess the biological relevance of the zinc requirement in Vif-Cul5 interaction and assess whether A3G retained antiviral function in the presence of 7 µM TPEN, we studied the effect of TPEN on virus infectivity. MAGI cells were infected with wild type or Vif deficient virus produced in 293T or 293T-A3G cells in the presence of 7 µM TPEN or control DMSO. We set the infectivity of WT virus in the absence of A3G to 100%, and calculated the relative infectivity under all treated conditions (FIG. 4). As expected, in the presence of A3G and the absence of Vif, there was a drastic decrease of infectivity to 8% (FIG. 4, lane 4). However in the presence of Vif, A3G was neutralized resulting in 91% infectivity (FIG. 4, lane 3). One would expect zinc chelation to have an effect on virus infectivity independent of Vif function. We observed a modest decrease in infectivity, of about 15% even in the absence of A3G (FIG. 4, lanes, 5 and 6). However, when we treat the producer cells with TPEN, in the presence of MG, Vif is no longer able to neutralize MG, resulting in an infectivity loss of about 87%, compared with an infectivity of 91% in the absence of TPEN (FIG. 4, compare lanes 3 and 7). These data demonstrate two important points; one, zinc is required for Vif function in the neutralization of MG, and two, that TPEN, at the concentrations used in this assay, has no effect on A3G function (FIG. 4, lanes 7 and 8).

Example IV

Preparatory Studies Prior to Testing in Human Subjects

In order to evaluate whether TPEN, its analogs, etc. will be effective in human subjects, efficacy and then safety are first evaluated in model systems. Since there is no good animal model for HIV efficacy studies, these preliminary studies will be done in vitro (in cell culture). Conventional methods will be used, employing the dosages, etc. as described herein. Animal safety (cytotoxicity) studies will be done, first in mice and then in larger non-primate animals. These cytotoxicity studies will yield data useful with respect to pharmacology, formulation and toxicology. Again, conventional methods will be used, employing dosages, modes of administration etc. as discussed herein. It is expected that the inhibitory agents of the invention, such as TPEN, will elicit few if any serious side effects (toxicity) in the test systems or in humans or other mammalian subjects, and that the inhibitory agents will elicit a therapeutic effect in humans having AIDS and/or in the early stages of HIV infection.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above and in the figures, are hereby incorporated in their entirety by reference.

We claim:

1. A method for inhibiting the infectivity of a lentivirus, comprising contacting a cell which is producing the virus with an antiviral-effective amount of a membrane-permeable Zinc (Zn) chelator, wherein the antiviral-effective amount of the Zn chelator does not substantially inhibit proteins in the cell which contain Zn-binding motifs other than the lentivirus Viral infectivity factor (Vif), and wherein the membrane-permeable Zn chelator is N,N,N',N'-Tetrakis-(2-pyridylmethyl) ethylenediamine (TPEN).

2. The method of claim 1, wherein the lentivirus expresses Vif.

3. The method of claim 1, wherein the antiviral-effective amount of TPEN is effectively between 4 and 12 μM.

4. The method of claim 1, wherein the antiviral-effective amount of TPEN is effectively between 4 and 9 μM.

5. The method of claim 1, wherein the antiviral-effective amount of TPEN is effectively 7 μM.

6. The method of claim 2, wherein the conditions are such that the membrane-permeable Zn chelator inhibits the interaction of the Vif protein with cellular Cullin 5-E3 ubiquitin ligase, thereby preventing the degradation of the viral inhibitor, Apobec3G, and thus allowing the Apobec3G to carry out its viral inhibiting function.

7. The method of claim 2, wherein the membrane-permeable Zn chelator interacts with the Zn-stabilized domain/motif H—$_{x2}$—YF—$_x$—CF—$_{x4}$-ϕ-$_{x2}$-A ϕ-$_{x7\text{-}8}$—C—$_{x3\text{-}5}$—H (SEQ ID NO:1) in the Vif protein.

8. The method of claim 1, which is carried out in cell culture.

9. The method of claim 1, which is carried out in a subject.

10. The method claim 1, wherein the lentivirus is SIV, SHIV, or HIV.

11. The method of claim 1, wherein the lentivirus which is inhibited is resistant to an inhibitor of reverse transcriptase, protease, integrase, entry of the virus into a cell, and/or assembly/maturation of the virus.

12. A method for inhibiting Vif protein activity in a cell, comprising contacting the protein with an inhibitory-effective amount of a membrane-permeable Zn chelator, wherein the inhibitory-effective amount of the Zn chelator does not substantially inhibit proteins in the cell which contain Zn-binding motifs other than Vif, and wherein the membrane-permeable Zn chelator is N,N,N',N'-Tetrakis-(2-pyridylmethyl)ethylenediamine (TPEN).

* * * * *

SEQUENCE LISTING

<160> NUMBER OF SEQ ID NOS: 4

<210> SEQ ID NO 1
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (9)..(12)
<223> OTHER INFORMATION: Variable amino acid
<220> FEATURE:
<221> NAME/KEY: MOD_RES
<222> LOCATION: (13)
<223> OTHER INFORMATION: Variable hydrophobic amino acid
<220> FEATURE:
<221> NAME/KEY: MOD_RES
<222> LOCATION: (14)..(15)
<223> OTHER INFORMATION: Variable amino acid
<220> FEATURE:
<221> NAME/KEY: MOD_RES
<222> LOCATION: (17)
<223> OTHER INFORMATION: Variable hydrophobic amino acid
<220> FEATURE:
<221> NAME/KEY: MOD_RES
<222> LOCATION: (18)..(25)
<223> OTHER INFORMATION: Variable amino acid, and this region may
      encompass 7-8 residues
<220> FEATURE:
<221> NAME/KEY: MOD_RES
<222> LOCATION: (27)..(31)
<223> OTHER INFORMATION: Variable amino acid, and this region may
      encompass 3-5 residues

<400> SEQUENCE: 1

His Xaa Xaa Tyr Phe Xaa Cys Phe Xaa Xaa Xaa Xaa Xaa Xaa Xaa Ala
 1               5                  10                  15

Xaa Xaa Xaa Xaa Xaa Xaa Xaa Xaa Xaa Cys Xaa Xaa Xaa Xaa Xaa His
                20                  25                  30

<210> SEQ ID NO 2
<211> LENGTH: 32
<212> TYPE: PRT
<213> ORGANISM: Human immunodeficiency virus 1

<400> SEQUENCE: 2

His Leu Tyr Tyr Phe Asp Cys Phe Ser Asp Ser Ala Ile Arg Lys Ala
 1               5                  10                  15

Leu Leu Gly His Ile Val Ser Pro Arg Cys Glu Tyr Gln Ala Gly His
                20                  25                  30

<210> SEQ ID NO 3
<211> LENGTH: 31
<212> TYPE: PRT
<213> ORGANISM: Simean immunodeficiency virus

```
<400> SEQUENCE: 3

His Cys His Tyr Phe Pro Cys Phe Thr Asp Arg Ala Ile Gln Gln Ala
 1               5                  10                  15

Ile Arg Gly Glu Ser Phe Leu Trp Cys Thr Tyr Lys Glu Gly His
            20                  25                  30

<210> SEQ ID NO 4
<211> LENGTH: 30
<212> TYPE: PRT
<213> ORGANISM: Simian immunodeficiency virus

<400> SEQUENCE: 4

His Asn Phe Tyr Phe Pro Cys Phe Thr Ala Arg Ala Val Asn Gln Ala
 1               5                  10                  15

Val Arg Gly Glu Leu Leu Thr Ser His Cys Trp Thr Pro His
            20                  25                  30
```